United States Patent [19]
Barrett et al.

[11] 3,934,032
[45] Jan. 20, 1976

[54] ALKANOLAMINE DERIVATIVES FOR TREATING HYPERTENSION

[75] Inventors: Arthur Michael Barrett, Leeds; John Carter, Macclesfield; Roy Hull, Macclesfield; David James Le Count, Macclesfield; Christopher John Squire, Macclesfield, all of England

[73] Assignee: Imperial Chemical Industries Limited, London, England

[22] Filed: Apr. 15, 1974

[21] Appl. No.: 461,262

Related U.S. Application Data

[60] Division of Ser. No. 233,781, March 10, 1972, Pat. No. 3,836,671, which is a continuation-in-part of Ser. No. 199,011, Nov. 15, 1971, abandoned, and Ser. No. 9,451, Feb. 6, 1970, Pat. No. 3,663,607.

[30] Foreign Application Priority Data

Feb. 21, 1969 United Kingdom................. 9445/69
Sept. 24, 1969 United Kingdom............... 47048/69
Nov. 19, 1970 United Kingdom............... 55028/70
Nov. 18, 1971 United Kingdom............... 53544/71

[52] U.S. Cl................................. 424/324; 424/324
[51] Int. Cl.$^2$......................................... A61K 27/00
[58] Field of Search..................................... 424/324

[56] References Cited
FOREIGN PATENTS OR APPLICATIONS

1,078,852   9/1967   United Kingdom................. 424/324

*Primary Examiner*—Frederick E. Waddell
*Attorney, Agent, or Firm*—Cushman, Darby & Cushman

[57] ABSTRACT

1-(electronegatively-substituted-alkyl- or alkenylphenoxy)-3-alkylamino-2-propanol derivatives, for example 1-p-carbamoylmethylphenoxy-3-isopropylamino-2-propanol, and pharmaceutical compositions containing them possess $\beta$-adrenergic blocking activity and are useful in the treatment of heart diseases and other complaints in man.

2 Claims, No Drawings

ALKANOLAMINE DERIVATIVES FOR TREATING HYPERTENSION

This application is a divisional application of Ser. No. 233,781, filed Mar. 10, 1972, now U.S. Pat. No. 3,836,671, which is a continuation-in-part of application Ser. No. 199,011, filed Nov. 15, 1971, now abandoned, and application Ser. No. 9451, filed Feb. 6, 1970, now U.S. Pat. No. 3,663,607.

This invention relates to new alkanolamine derivatives which possess β-adrenergic blocking activity.

According to the invention there is provided a new alkanolamine derivative selected from compounds of the formula:

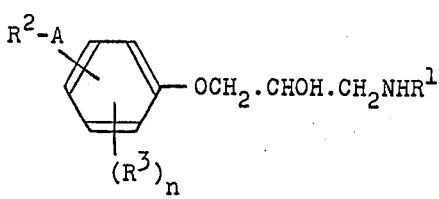

wherein $R^1$ is alkyl or hydroxyalkyl each of up to 6 carbon atoms; wherein either:

A is alkylene of 1 to 5 carbon atoms and $R^2$ is alkanoyl of up to 6 carbon atoms, carbamoyl or carbazoyl, or alkyl-carbamoyl or alkenylcarbamoyl each of up to 7 carbon atoms; or A is alkenylene of 2 to 5 carbon atoms and $R^2$ is alkanoyl or alkoxycarbonyl each of up to 6 carbon atoms, cyano, carbamoyl or carbazoyl, or alkylcarbamoyl or alkenylcarbamoyl each of up to 7 carbon atoms;

wherein n is the integer 1 or 2; and wherein $R^3$, the values of which may be the same or different when n is 2, is selected from hydrogen, halogen, nitro, hydroxy, cyano, phenyl, phenoxy, benzyl, α-phenylethyl, benzyloxy, cycloalkyl of up to 8 carbon atoms, alkyl, alkenyl, alkanoyl and alkoxycarbonyl each of up to 6 carbon atoms, alkylthio, alkoxy and alkenyloxy each of up to 5 carbon atoms, and alkyl of up to 5 carbon atoms which is substituted by hydroxy, alkoxy of up to 4 carbon atoms or halogen;

and the non-toxic, pharmaceutically-acceptable acidaddition salts thereof.

It is to be understood that the above definition of alkanolamine derivatives encompasses all possible stereoisomers thereof, and mixtures thereof, which possess β-adrenergic blocking activity, and in particular it encompasses racemic mixtures and any optical isomer which possesses β-adrenergic blocking activity.

A suitable value for $R^1$ is, for example, alkyl or hydroxyalkyl each of 3, 4 or 5 carbon atoms, which preferably is branched at the α-carbon atom, for example isopropyl, s-butyl, t-butyl, 2-hydroxy-1,1-dimethylethyl or 2-hydroxy-1-methylethyl. Particularly preferred values for $R^1$ are isopropyl and t-butyl.

A suitable value for $R^2$ is for example, acetyl, propionyl, methoxycarbonyl, ethoxycarbonyl, cyano, carbamoyl, carbazoyl, methylcarbamoyl, isopropylcarbamoyl, n-butylcarbamoyl or allylcarbamoyl.

A suitable value for A is, for example, methylene, ethylene, ethylidene

trimethylene or vinylene.

A suitable value for $R^3$ is, for example, hydrogen, fluorine, chlorine, bromine, iodine, nitro, hydroxy, cyano, phenyl, phenoxy, benzyl, α-phenylethyl, benzyloxy, cyclopropyl, cyclobutyl, cyclopentyl, methyl, n-propyl, s-butyl, allyl, acetyl, propionyl, methoxycarbonyl, ethoxycarbonyl, methylthio, methoxy, isopropoxy, allyloxy, hydroxymethyl, methoxymethyl or trifluoromethyl.

Suitable non-toxic, pharmaceutically-acceptable acid-addition salts of the alkanolamine derivatives of the invention are, for example, salts derived from inorganic acids, for example hydrochlorides, hydrobromides, phosphates or sulphates, or salts derived from organic acids, for example oxalates, lactates, tartrates, acetates, salicylates, citrates, benzoates, β-naphthoates, adipates or 1,1-methylene-bis-(2-hydroxy-3-naphthoates), or salts derived from acidic synthetic resins, for example sulphonated polystyrene resins, for example "Zeo-Karb" 225 ("Zeo-Karb" is a Trade Mark).

One preferred alkanolamine derivative of the invention is selected from compounds of the formula:

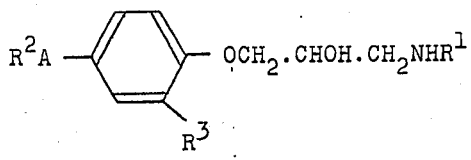

wherein $R^1$, $R^2$, A and $R^3$ have the meanings stated above, and the non-toxic, pharmaceutically-acceptable acid-addition salts thereof. A particularly preferred derivative is selected from compounds of the latter formula given above wherein $R^1$ is isopropyl or t-butyl and wherein either a. $R^2$ is carbamoyl or alkylcarbamoyl of up to 4 carbon atoms, A is methylene and $R^3$ is hydrogen, halogen or alkyl, alkenyl or alkoxy each of up to 4 carbon atoms; or b. $R^2$ is acetyl or carbamoyl, A is ethylene or vinylene and $R^3$ is alkoxy of up to 4 carbon atoms; or c. $R^2$ is cyano, A is vinylene and $R^3$ is alkoxy of up to 4 carbon atoms; and the non-toxic, pharmaceutically-acceptable acid-addition salts thereof.

A second preferred alkanolamine derivative of the invention is selected from compounds of the formula:

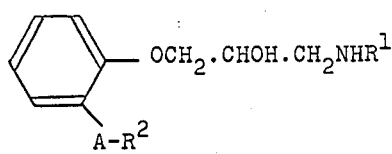

wherein $R^1$ and $R^2$ have the meanings stated above and wherein A is alkenylene of 2 to 5 carbon atoms, and the non-toxic pharmaceutically-acceptable acid-addition salts thereof. A particularly preferred derivative is selected from compounds of the last-mentioned formula given above wherein $R^1$ is isopropyl or t-butyl, $R^2$ is cyano or carbamoyl and A is vinylene, and the non-toxic pharmaceutically-acceptable acid-addition salts thereof.

Specific alkanolamine derivatives of the invention are, for example, those hereinafter described in the Examples. Of these, particularly active compounds are 1-p-carbamoylmethylphenoxy-3-isopropylamino-2-propanol; 1-p-(N-isopropylcarbamoylmethyl)phenoxy-3-isopropylamino-2-propanol; 1-(2-bromo-4-carbamoylmethylphenoxy)-3-isopropylamino-2-propanol; 1-p-carbamoylmethylphenoxy-3-t-butylamino-2-propanol; 1-m-carbamoylmethylphenoxy-3-isopropylamino-2-propanol; 1-(2-allyl-4-carbamoylmethylphenoxy)-3-isopropylamino-2-propanol; 1-(4-carbamoylmethyl-2-methoxyphenoxy)-3-isopropylamino-2-propanol; 1-p-(N-methylcarbamoylmethyl)phenoxy-3-isopropylamino-2-propanol; 1-(4-carbamoylmethyl-2-iodophenoxy)-3-isopropylamino-2-propanol; 1-(2-chloro-4-carbamoylmethyl-phenoxy)-3-isopropylamino-2-propanol; 1-(2-chloro-4-carbamoylmethylphenoxy)-3-t-butylamino-2-propanol; 1-(2-fluoro-4-carbamoylmethylphenoxy)-3-isopropylamino-2-propanol; 1-(2-fluoro-4-carbamoylmethylphenoxy)-3-t-butylamino-2-propanol; 1-(4-carbamoylmethyl-2-methylphenoxy)-3-isopropylamino-2-propanol; 1-(4-carbamoylmethyl-2-n-propylphenoxy)-3-isopropylamino-2-propanol; 1-(4-carbamoylmethyl-2-s-butylphenoxy)-3-isopropylamino-2-propanol; 1-(4-carbamoylmethyl-2-methoxyphenoxy)-3-t-butylamino-2-propanol; 1-(4-N-methylcarbamoylmethyl-2-n-propylphenoxy)-3-isopropylamino-2 -propanol; 1-(2-allyl-4-N-methylcarbamoylmethylphenoxy)-3-isopropylamino2-propanol; 1-(2-allyl-4-N-methylcarbamoylmethylphenoxy)-3-t-butylamino-2-propanol; 1-(4-carbamoylmethyl-2,5-dimethylphenoxy)-3-isopropylamino-2-propanol; 1-(4-$\beta$-carbamoylethyl2-methoxyphenoxy)-3-isopropylamino-2-propanol; 1-(4-$\beta$-carbamoylethyl-2-methoxyphenoxy)-3-t-butylamino-2-propanol; 1-[2-methoxy-4-(3-oxobutyl)-phenoxy]-3-isopropylamino-2-propanol; 1-(2-methoxy-4-$\beta$-methoxycarbonylvinylphenoxy)-3-isopropylamino-2-propanol- 1-(4-$\beta$-cyanovinyl-2-methoxyphenoxy)-3-isopropylamino-2-propanol; 1-(4-$\beta$-carbamoylvinyl-2-methoxy-phenoxy)-3-isopropylamino-2-propanol; 1-[2-methoxy-4-(3-oxobut-1-enyl)phenoxy]-3-t-butylamino-2-propanol; 1-(2-$\beta$-cyanovinylphenoxy)-3-t-butylamino-2-propanol and 1-(2-$\beta$-carbamoylvinylphenoxy)-3-isopropylamino-2-propanol and the non-toxic, pharmaceutically-acceptable acid-addition salts thereof.

The alkanolamine derivatives of the invention may be prepared by conventional chemical means. One preferred process for the manufacture of the alkanolamine derivatives comprises the reaction of a compound of the formula:

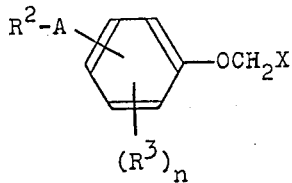

wherein $R^2$, A, $R^3$ and n have the meanings stated above, and wherein X stands for the group

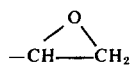

or the group —CHOH.CH$_2$Y, wherein Y stands for a halogen atom, or of mixtures of such compounds wherein X has both meanings stated above, with an amine of the formula NH$_2$R$^1$, wherein R$^1$ has the meaning stated above.

A suitable value for Y is, for example, the chlorine or bromine atom. The reaction may be carried out at ambient temperature or it may be accelerated or completed by the application of heat, for example by heating to a temperature of 90°–110°C.; it may be carried out at atmospheric or at an elevated pressure, for example by heating in a sealed vessel; and it may be carried out in an inert diluent or solvent, for example methanol or ethanol, or an excess of the amine of the formula NH$_2$R$^1$, wherein R$^1$ has the meaning stated above, may be used as diluent or solvent.

The starting material used in the above process may be obtained by the reaction of the corresponding phenol with an epihalohydrin, for example epichlorohydrin. The said starting material may be isolated or it may be prepared and used in situ without isolation.

The alkanolamine derivatives of the invention in free base form may be converted into non-toxic, pharmaceutically acceptable acid-addition salts thereof by reaction with a suitable acid by conventional means.

As stated above, the alkanolamine derivatives of the invention and the non-toxic, pharmaceutically acceptable acid-addition salts thereof possess $\beta$-adrenergic blocking activity. Furthermore, many of these compounds possess selective $\beta$-adrenergic blocking activity. Compounds exhibiting this selective action show a greater degree of specificity in blocking the cardiac $\beta$-receptors than the $\beta$-receptors in peripheral blood vessels and bronchial muscle. Thus, a dose may be selected for such a compound at which the compound blocks the cardiac inotropic and chronotropic actions of a catecholamine [for example isoprenaline, that is, 1-(3,4-dihydroxyphenyl)-2-isopropylaminoethanol] but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the selective compound will substantially inhibit the unwanted stimulatory effects of the bronchodilator on the heart but will not hinder the desirable therapeutic effect of the bronchodilator.

Many compounds possessing $\beta$-adrenergic blocking activity are known, many of these being 1-aryloxy-3-amino-2-propanol derivatives, and it is also known that some of these compounds, especially those wherein the 1-aryloxy radical bears an acylamino substituent, possess selective $\beta$-adrenergic blocking activity. It is a desirable, although not absolutely essential, feature of a $\beta$-adrenergic blocking agent which is to be used clinically that the agent does not possess any substantial amount of intrinsic sympathomimetic activity. The compound with which most clinical experience has been obtained, propranolol [1-isopropylamino-3-(naphth-1-yloxy)-2-propanol], which is described and claimed in U.S. Pat. No. 3,337,628 is totally devoid of intrinsic sympathomimetic activity. However, no compound which possesses selective $\beta$-adrenergic blocking activity as defined above is known which is devoid of intrinsic sympathomimetic activity. In particular, the selective β-adrenergic blocking agent with which most clinical experience has been obtained, practolol [1-(4-acetamidophenoxy)-3-isopropylamino2-propanol, which is described and claimed in U.S. Pat. No. 3,408,387], possesses significant intrinsic sympathomimetic activity.

We have now found that many of the compounds of the present invention, and especially the compounds 1-p-carbamoylmethylphenoxy-3-isopropylamino-2-propanol and 1-(4-β-carbamoylethyl-2-methoxyphenoxy)-3-isopropylamino-2-propanol, possess selective β-adrenergic blocking activity as determined by the inhibition of isoprenaline-induced tachycardia in cats, and by freedom from antagonism of isoprenaline-induced vasodilatation in cats or of the relief produced by isoprenaline of histamineinduced bronchospasm in guinea-pigs. These compounds are, however, devoid of intrinsic sympathomimetic activity as demonstrated by their failure to increase the heart rate of rats from which natural catecholamines have been depleted by pre-treatment with syrosingopine. The β-adrenergic blocking activity in cats and rats of the compounds is quantitatively similar to that of practolol, and at doses of the compounds which produce effective β-adrenergic blockade in cats and rats there is no evidence of toxicity.

According to a further feature of the invention there is provided a pharmaceutical composition comprising as active ingredient at least one alkanolamine derivative of the invention, or a non-toxic, pharmaceutically-acceptable acid-addition salt thereof, in association with a pharmaceutically acceptable diluent or carrier therefor.

Suitable compositions are, for example, tablets, capsules, aqueous or oily solutions or suspensions, emulsions, injectable aqueous or oily solutions or suspensions, dispersible powders, sprays or aerosol formulations.

The pharmaceutical compositions of the invention may contain, in addition to the alkanolamine derivative of the invention, one or more drugs selected from sedatives, for example phenobarbitone, meprobamate and chlorpromazine; vasodilators, for example glyceryl trinitrate, pentaerythritol tetranitrate and isosorbide dinitrate; diuretics, for example chlorothiazide; hypotensive agents, for example reserpine, bethanidine and guanethidine; myocardial depressants, for example quinidine; agents used in the treatment of Parkinson's disease, for example benzhexol; cardiotonic agents, for example digitalis preparations; and sympathomimetic bronchodilators, for example isoprenaline, orciprenaline, adrenaline and ephedrine.

When the alkanolamine derivatives of the invention are to be used in man, for example for the treatment of heart diseases such as angina pectoris and cardiac arrythmias, or for the treatment of hypertension or phaeochromocytoma, it is expected that they would be given at a total oral dose of between 25 mg. and 1,200 mg. daily, preferably between 200 mg. and 600 mg. daily, at doses spaced at 6–8 hourly intervals, or at an intravenous dose of between 1 mg. and 40 mg., preferably between 5 mg. and 25 mg. Preferred oral dosage forms are tablets or capsules containing between 25 and 200 mg., and preferably 100 mg., of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.2% w/v of active ingredient.

The invention is illustrated but not limited by the following Examples:

EXAMPLE 1

A solution of 1 g. of 1-p-carbamoylmethylphenoxy-2,3-epoxypropane and 10 ml. of isopropylamine in 25 ml. of methanol is heated in a sealed tube at 110°C. for 12 hours. The mixture is evaporated to dryness and the residue is partitioned between 50 ml. of chloroform and 50 ml. of aqueous 2N-hydrochloric acid. The aqueous acidic layer is separated, made alkaline with sodium carbonate and extracted twice with 50 ml. of chloroform each time. The combined extracts are dried and evaporated to dryness and the residue is crystallised from ethyl acetate. There is thus obtained 1-p-carbamoylmethylphenoxy-3-isopropylamino-2-propanol, m.p. 146°–148°C.

The 1-p-carbamoylmethylphenoxy-2,3-epoxypropane used as starting material may be obtained as follows:

A mixture of 3.2 g. of p-hydroxyphenylacetamide, 25 ml. of epichlorohydrin and 6 drops of piperidine is heated at 95°–100°C. for 6 hours. The mixture is cooled and filtered and the solid product is crystallised from methanol. There is thus obtained 1-p-carbamoylmethylphenoxy-2,3-epoxypropane, m.p. 158°–160°C.

EXAMPLE 2

By a process substantially similar to that described in Example 1, using the appropriate phenol, epichlorohydrin and the appropriate amine as starting materials, there are obtained the compounds described in the following tables:

TABLE 1

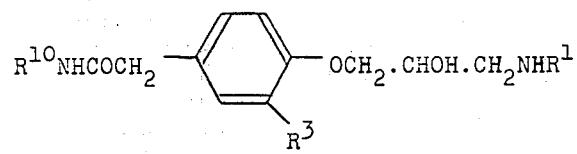

$R^{10}NHCOCH_2$ —⟨phenyl with $R^3$⟩— $OCH_2.CHOH.CH_2NHR^1$

| $R^{10}$ | $R^3$ | $R^1$ | m.p. (°C.) |
|---|---|---|---|
| H | methoxy | isopropyl | 118–120 |
| H | methoxy | t-butyl | 87–89 |
| H | iodo | isopropyl | 126–128 |
| H | methyl | isopropyl | 126–127 |
| H | s-butyl | isopropyl | hydrogen oxalate 124–130 |
| H | n-propyl | isopropyl | 116–117 |
| n-butyl | H | isopropyl | 115–117 |
| n-butyl | H | t-butyl | oxalate 211–213 |
| allyl | H | isopropyl | 112–114 |
| methyl | allyl | isopropyl | 106–108 |
| methyl | allyl | t-butyl | oxalate 187–189 |
| allyl | allyl | isopropyl | 94–96 |
| isopropyl | H | isopropyl | 132–134 |
| H | H | 1-methyl-2-hydroxyethyl | 134–136 |
| isopropyl | nitro | t-butyl | 117–119 |
| H | bromo | isopropyl | 105–107 |
| H | allyl | isopropyl | hydrogen oxalate 101–102 |
| methyl | H | isopropyl | 87–89 |
| H | H | t-butyl | 119–120 |
| methyl | n-propyl | isopropyl | 125–127 |
| H | fluoro | isopropyl | 97–100 |
| H | fluoro | t-butyl | 92–95 |
| H | chloro | t-butyl | 100–101 |

-continued

| R[10] | R[3] | R[1] | m.p. (°C.) |
|---|---|---|---|
| H | chloro | isopropyl | 101–102 |

TABLE 2

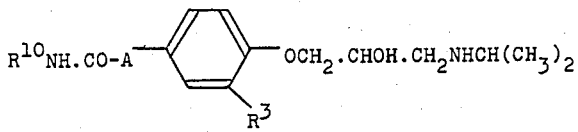

$R^{10}NH.CO-A$ —⟨benzene ring with $R^3$⟩— $OCH_2.CHOH.CH_2NHCH(CH_3)_2$

| R[10] | A | R[3] | m.p. (°C.) |
|---|---|---|---|
| H | —CH$_2$CH$_2$— | bromo | 102–104 |
| H | —CH$_2$CH$_2$CH$_2$— | bromo | 69–71 |
| H | —CH$_2$CH$_2$— | nitro | 130–132 |
| H | —CH(CH$_3$)— | H | 101–104 |
| H | —CH$_2$CH$_2$— | allyl | 93–95 |
| H | —CH$_2$CH$_2$CH$_2$— | allyl | 78–80 |
| isopropyl | —CH$_2$CH$_2$— | nitro | 108–110 |
| H | —CH=CH— | methoxy | 138–140 |
| isopropyl | —CH=CH— | methoxy | 123–125 |
| H | —CH$_2$CH$_2$CH$_2$— | H | 85–87 |
| H | —CH$_2$CH$_2$— | methoxy | 108–109 |
| H | —CH=CH— | H | 135–137 |
| H | —CH$_2$CH$_2$— | H | 102–104 |

There are also prepared, by a similar process to that described in Example 1 using the appropriate starting materials, 1-m-carbamoylmethylphenoxy-3-isopropylamino-2-propanol, m.p. 82°–84°C.; 1-o-carbamoylmethylphenoxy-3-isopropylamino-2-propanol hydrogen oxalate, m.p. 146°–148°C.; 1-(4-carbamoylmethyl-3-methylphenoxy)-3-isopropylamino-2-propanol, m.p. 132°–134°C.; 1-(4-carbamoylmethyl-2,3-dimethylphenoxy)-3-ispropylamino-2-propanol hydrogen oxalate, m.p. 213°–215°C.; 1-(4-carbamoylmethyl-2,5-dimethylphenoxy)-3-isopropylamino-2-propanol, m.p. 111°–113°C.; 1-(2-β-carbamoylvinylphenoxy)-3-isopropylamino-2-propanol, m.p. 144°–146°C. and 1-(4-β-carbamoylethyl-2-methoxyphenoxy)-3-t-butylamino-2-propanol hydrogen oxalate, m.p. 148°–149°C.

EXAMPLE 3

A solution of 0.75 g. of 3-isopropylamino-1-p-methoxycarbonylmethylphenoxy-2-propanol in 3 ml. of 63% aqueous hydrazine hydrate is heated at 95°–100°C. for 2 hours. 20 Ml. of water are added and the mixture is extracted twice with 30 ml. of chloroform each time. The combined chloroform solutions are dried and evaporated to dryness and the residue is crystallised from a mixture of ethyl acetate and petroleum ether (b.p. 60°–80°C.). There is thus obtained 1-p-carbazoylmethylphenoxy-3-isopropylamino-2-propanol, m.p. 92°–93°C.

The 3-isopropylamino-1-p-methoxycarbonylmethylphenoxy2-propanol used as starting material may be obtained as follows:

A solution of 0.5 g. of 1-p-carbamoylmethylphenoxy-3-isopropylamino-2-propanol in 50 ml. of methanol is saturated with anhydrous hydrogen chloride and is heated under reflux for 3 hours. The solution is evaporated to dryness, the residue is dissolved in water and the solution is basified with sodium carbonate. The basic solution is extracted twice with 30 ml. of chloroform each time and the combined chloroform extracts are dried and evaporated to dryness. The residue is crystallised from petroleum ether (b.p. 60°–80°C.) and there is thus obtained 3-isopropylamino1-p-methoxycarbonylmethylphenoxy-2-propanol, m.p. 65°–67°C.

EXAMPLE 4

A mixture of 1.18 g. of 1-p-formylphenoxy-3-isopropylamino-2-propanol, 0.5 g. of methyl hydrogen malonate, 15 ml. of pyridine and 5 drops of piperidine is heated at 95°–100°C. for 16 hours, cooled and evaporated to dryness under reduced pressure. The residue is crystallised from a mixture of ethyl acetate and petroleum ether (b.p. 60°–80°C.) and there is thus obtained 3-isopropylamino-1-p-(β-methoxycarbonylvinyl)-phenoxy-2-propanol, m.p. 90°–92°C.

The 1-p-formylphenoxy-3-isopropylamino-2-propanol used as starting material may be obtained as follows:

A mixture of 5 g. of 3-chloro-1-p-formylphenoxy-2-propanol and 50 ml. of aqueous N-sodium hydroxide solution is shaken for 4 hours and then extracted twice with 100 ml. of chloroform each time. The combined chloroform extracts are dried and evaporated to dryness under reduced pressure and the residual oil, which consists essentially of 2,3-epoxy-1-(p-formylphenoxy)-propane, is immediately dissolved in 50 ml. of isopropylamine. The solution is heated under reflux for 16 hours, cooled and evaporated to dryness. The residue slowly solidifies, and is crystallised from a mixture of benzene and petroleum ether (b.p. 60°–80°C.). There is thus obtained 3-isopropylamino-1-p-(N-isopropyliminomethyl)phenoxy-2-propanol, m.p. 81°–83°C.

A mixture of the above propanol and 150 ml. of aqueous 6N-hydrochloric acid is heated under reflux for 4 hours and then evaporated to dryness under reduced pressure. The residue is dissolved in water, the solution is made alkaline with solid sodium carbonate and the mixture is extracted with ethyl acetate. The extract is dried and evaporated to dryness and the residue is crystallised from a mixture of benzene and petroleum ether (b.p. 60°–80°C.). There is thus obtained 1-p-formylphenoxy-3-isopropylamino-2-propanol, m.p. 86°–88°C.

EXAMPLE 5

Sufficient methanol to give a clear solution is added to a suspension of 5.2 g. of 1-[2-methoxy-4-(3-oxobut-1-enyl)phenoxy]-2,3-epoxypropane in 100 ml. of t-butylamine, and the solution is kept at room temperature for 3 days and is then evaporated to dryness. The residue is crystallised from a mixture of ethyl acetate and petroleum ether (b.p. 60°–80°C.) and there is thus obtained 1-[2-methoxy-4-(3-oxobut-1-enyl)-phenoxy]-3-t-butylamino-2-propanol, m.p. 62°–64°C.

The 1-[2-methoxy-4-(3-oxobut-1-enyl)phenoxy]-2,3,-epoxypropane used as starting material may be obtained as follows:

A mixture of 12.5 g. of vanillin (4-hydroxy-3-methoxybenzaldehyde), 50 ml. of acetone and 40 ml. of 9% aqueous sodium hydroxide solution is kept at room temperature for 30 days. 100 Ml. of water are added, the excess of acetone is removed by evaporation under reduced pressure and the residue is acidified with 20% aqueous acetic acid solution. The mixture is filtered and the solid product is crystallised from aqueous ethanol. There is thus obtained 4-(4-hydroxy-3-methoxyphenyl)but-3-en-2-one, m.p. 119°–122°C.

A mixture of 11.3 g. of the above product, 110 ml. of epichlorohydrin and 6 drops of piperidine is heated at 90-95°C. for 6 hours. The excess of epichlorohydrin is removed by evaporation under reduced pressure and the residue is stirred with 200 ml. of N-aqueous sodium hydroxide solution at room temperature for 3 hours. The mixture is filtered and the solid product is crystallised from benzene. There is thus obtained 1-[2-methoxy-4-(3-oxobut-1-enyl)phenoxy]-2,3-epoxypropane, m.p. 109-112°C.

EXAMPLE 6

The process described in Example 5 is repeated except that 1-[2-methoxy-4-(3-oxobutyl)phenoxy]-2,3-epoxypropane and isopropylamine are used as starting materials. There is thus obtained 1-[2-methoxy-4-(3-oxobutyl)phenoxy]-3-isopropylamino-2-propanol, m.p. 71°–72°C.

The 1-[2-methoxy-4-(3-oxobutyl)phenoxy]-2,3-epoxypropane (b.p. 168°C./0.6 mm.) used as starting material may be obtained by a similar process to that described in the last part of Example 5, except that 4-(4-hydroxy-3-methoxyphenyl)-butan-2-one [b.p. 126°C./0.4 mm., prepared by hydrogenation of 4-(4-hydroxy-3-methoxyphenyl)-but-3-en-2-one in ethanol solution at room temperature and atmospheric pressure, using Raney nickel as catalyst] is used as starting material.

EXAMPLE 7

A mixture of 1.33 g. of 3-isopropylamino-1-(4-formyl2-methoxyphenoxy)-2-propanol, 1.18 g. of methyl hydrogen malonate, 15 ml. of pyridine and 5 drops of piperidine is heated at 95°–100°C. for 72 hours. The pyridine is removed by evaporation and the residue is partitioned between 30 ml. of chloroform and 30 ml. of dilute aqueous potassium carbonate solution. The chloroform layer is separated, dried and evaporated to dryness and the residue is crystallised from petroleum ether (b.p. 60°–80°C.). There is thus obtained 3-isopropylamino-1-(2-methoxy-4-β-methoxycarbonylvinylphenoxy)-2-propanol, m.p. 79°–80°C.

The process described above is repeated except that ethyl hydrogen malonate is used as starting material in place of methyl hydrogen malonate. There is thus obtained 1-(4-β-ethoxycarbonylvinyl-2-methoxyphenoxy)-3-isopropylamino-2-propanol as a colourless oil.

The 3-isopropylamino-1-(4-formyl-2-methoxyphenoxy)-2-propanol used as starting material may be obtained as follows:

A mixture of 50 g. of vanillin, 77 ml. of epichlorohydrin and 0.33 g. of piperidine hydrochloride is heated at 95°–100°C. for 4 hours. The excess epichlorohydrin is removed by evaporation under reduced pressure and the residue is distilled at 178°–183°C./0.6-0.7 mm. The distilled product is stirred rapidly with 400 ml. of aqueous N-sodium hydroxide solution for 4 hours, and the solid is extracted from the mixture with 400 ml. of chloroform. The chloroform solution is dried and evaporated to dryness and there is thus obtained as residue 1-(4-formyl-2-methoxyphenoxy)-2,3-epoxypropane, a pale yellow solid which is used without further purification. A solution of 5 g. of 1-(4-formyl-2-methoxyphenoxy)-2,3-epoxypropane and 50 ml. of isopropylamine in 50 ml. of chloroform is heated under reflux for 18 hours. The mixture is evaporated to dryness and the residue is crystallised from a mixture of benzene and petroleum ether (b.p. 60°–80°C.). There is thus obtained 1-[2-methoxy-4-(N-isopropyliminomethyl)phenoxy]-3-isopropylamino-2-propanol. A mixture of the above compound, 75 ml. of concentrated aqueous hydrochloric acid and 75 ml. of water is heated under reflux for 4 hours. The aqueous hydrochloric acid is removed by evaporation and the residue is partitioned between 100 ml. of chloroform and 100 ml. of aqueous 2N-hydrochloric acid. The aqueous acidic layer is separated, made alkaline with sodium carbonate and extracted twice with 100 ml. of chloroform each time. The combined extracts are dried and evaporated to dryness. The residual basic oil is converted to the oxalate thereof by conventional means, and the oxalate is crystallised from a mixture of methanol and water. The oxalate is reconverted to the free base by conventional means, and the base is crystallised from a mixture of ethyl acetate and petroleum ether (b.p. 60°–80°C.). There is thus obtained 3-isopropylamino-1-(4-formyl-2-methoxyphenoxy)-2-propanol, m.p. 56°–58°C.

EXAMPLE 8

A solution of 2.5 g. of 1-(2-β-cyanovinylphenoxy)-3-chloro-2-propanol and 25 ml. of t-butylamine in 25 ml. of n-propanol is heated at 95°–100°C. for 5 hours. The mixture is evaporated to dryness and the residue is partitioned between 50 ml. of chloroform and 100 ml. of aqueous 20% hydrochloric acid. The aqueous acidic layer is separated, made alkaline with aqueous sodium hydroxide solution and extracted three times with 50 ml. of chloroform each time. The combined extracts are dried and evaporated to dryness and the residue is dissolved in 5 ml. of chloroform. The solution is added to a 90 cm. × 2.5 cm. chromatography column of silica gel ('Florisil'; 'Florisil' is a Trade Mark) and the column is eluted successively with chloroform, a 1:1 v/v mixture of chloroform and ethyl acetate, ethyl acetate and an 80:15:5 v/v mixture of ethyl acetate, ethanol and triethylamine. The relevant fraction is evaporated to dryness and the residue is crystallised from cyclohexane. There is thus obtained 1-(2-β-cyanovinylphenoxy)-3-t-butylamino-2-propanol, m.p. 76°–78°C.

The 1-(2-β-cyanovinylphenoxy)-3-chloro-2-propanol used as starting material may be obtained as follows:

A mixture of 2.0 g. of 2-(β-cyanovinyl)phenol, 25 ml. of epichlorohydrin and 4 drops of piperidine is heated at 95°–100°C. for 4 hours and then evaporated to dryness. The residual oil consists of the desired starting material and is used without further purification.

EXAMPLE 9

The process described in Example 8 is repeated except that 1-(4-β-cyanovinyl-2-methoxyphenoxy)-3-chloro-2-propanol and isopropylamine are used as starting materials. There is thus obtained 1-(4-β-cyanovinyl-2-methoxyphenoxy)-3-isopropylamino-2-propanol, m.p. 102°–104°C.

EXAMPLE 10

A solution of 50 parts by weight of stearic acid in 160 parts by weight of methylated spirit is added to a mixture of 200 parts by weight of calcium phosphate, 100 parts by weight of 1-p-carbamoylmethylphenoxy-3-isopropylamino-2-propanol and 40 parts by weight of maize starch to form a paste suitable for granulation.

The paste is passed through a 12-mesh screen and the granules are dried at a temperature not exceeding 60°C. 9 Parts by weight of calcium carboxymethylcellulose, 4.5 parts by weight of magnesium stearate and 46.5 parts by weight of maize starch are added, and the mixture is passed through a 20-mesh screen. The resultant granules are reblended and compressed into tablets each weighing 450 mg. and containing 100 mg. of active ingredient.

EXAMPLE 11

The process described in Example 10 is repeated except that the proportions of calcium phosphate, 1-p-carbamoylmethylphenoxy-3-isopropylamino-2-propanol and maize starch in the initial mixture are 340, 50 and 30 parts by weight respectively, and that 36.5 in place of 46.5 parts by weight of maize starch are added at the later stage. There are thus obtained tablets each weighing 520 mg. and containing 50 mg. of active ingredient.

EXAMPLE 12

A tablet prepared according to Example 10 or 11 is film-coated by conventional means using a coating suspension containing 9.9 parts by weight of hydroxypropyl methylcellulose, 2.5 parts by weight of ethylcellulose, 1.9 parts by weight of glycerin, 0.6 parts by weight of stearic acid and 3.1 parts by weight of titanium dioxide suspended in a mixture of equal parts by volume of dichloromethane and isopropyl alcohol. There are thus obtained coated tablets suitable for oral administration to man for therapeutic purposes.

EXAMPLE 13

1-p-Carbamoylmethylphenoxy-3-isopropylamino-2-propanol (0.5 g.) is dissolved in a solution of citric acid (5 g.) in water for injection (800 ml.) and the solution is adjusted to pH 6 with a freshly-prepared 4% w/v solution of sodium hydroxide in water for injection. The volume of the solution is made up to 1 liter and the solution is then passed through a bacterial filter and filled into clean 10 ml. neutral glass ampoules. The ampoules are fusion-sealed and sterilised by heating at 115°–116°C. for 30 minutes. There is thus obtained a sterile injectable aqueous solution suitable for parenteral administration to man for therapeutic purposes.

The 1-p-carbamoylmethylphenoxy-3-isopropylamino-2-propanol used as active ingredient in the pharmaceutical compositions described in any of Examples 10 to 13 may be replaced by any of the compounds hereinbefore described in any of Examples 2 to 9, and there are similarly obtained pharmaceutical compositions suitable for administration to man for therapeutic purposes.

What we claim is:

1. A method for the treatment of hypertension in a warm-blooded animal in need of such treatment which comprises administering orally, parenterally or by inhalation to said animal an effective amount of at least one alkanolamine derivative selected from the group consisting of a compound of the formula:

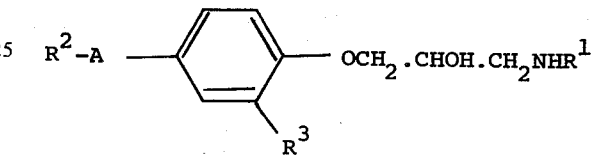

wherein $R^1$ is isopropyl or t-butyl, $R^2$ is carbamoyl or alkylcarbamoyl of up to 4 carbon atoms, A is alkylene of 1 to 5 carbon atoms or alkenylene of 2 to 5 carbon atoms and $R^3$ is hydrogen, halogen or alkyl, alkenyl or alkoxy each of up to 4 carbon atoms; and a non-toxic, pharmaceutically acceptable acid-addition salt thereof.

2. The method of claim 1 wherein the alkanolamine derivative is 1-p-carbamoylmethylphenoxy-3-isopropylamino-2-propanol or a non-toxic, pharmaceutically acceptable acid-addition salt thereof.

* * * * *